(12) United States Patent
Suh et al.

(10) Patent No.: US 6,237,419 B1
(45) Date of Patent: May 29, 2001

(54) ASPHERICAL CURVED ELEMENT TRANSDUCER TO INSPECT A PART WITH CURVED ENTRY SURFACE

(75) Inventors: Ui W. Suh; Douglas E. Ingram, both of Cincinnati; Richard E. Klaassen; Walter J. Bantz, both of West Chester, all of OH (US)

(73) Assignee: General Electric Company, Cincinnati, OH (US)

( * ) Notice: Subject to any disclaimer, the term of this patent is extended or adjusted under 35 U.S.C. 154(b) by 0 days.

(21) Appl. No.: 09/374,531

(22) Filed: Aug. 16, 1999

(51) Int. Cl.$^7$ .............................. G01N 3/00; H01L 41/04
(52) U.S. Cl. .............................. 73/642; 73/1.82; 73/632; 310/334
(58) Field of Search .................... 310/334, 335, 310/336; 73/642, 632, 1.82, 644, 865.9, 866.5, 432.1, 602

(56) References Cited

U.S. PATENT DOCUMENTS

| 4,276,779 | * | 7/1981 | Davis, Jr. ............................... 73/626 |
| 4,395,652 | * | 7/1983 | Nakanishi et al. .................... 310/334 |
| 4,726,231 | * | 2/1988 | Tretout et al. ......................... 73/644 |
| 4,888,746 | * | 12/1989 | Wurster et al. ....................... 367/138 |
| 5,003,516 | * | 3/1991 | Sato et al. ............................ 367/150 |
| 5,640,961 | * | 6/1997 | Verdonk ............................... 600/459 |

* cited by examiner

*Primary Examiner*—Hezron Williams
(74) *Attorney, Agent, or Firm*—Andrew C. Hess; Gerry S. Gressel

(57) ABSTRACT

An ultrasonic inspection element and method of fabrication are provided for ultrasonic inspection of curved surface parts. Various points on a transducer are located. These points include the location where a ray starts, to the desired focal point in the material being inspected. The path of the ray is through a water medium and a water-metal boundary. These points are fitted onto a cylindrical surface. The ray is back propagated until it is focused at the desired focal point.

11 Claims, 4 Drawing Sheets

ASPHERICAL CURVED ELEMENT TRANSDUCER TO INSPECT A PART WITH CURVED ENTRY SURFACE

BACKGROUND OF THE INVENTION

The present invention relates to the design of ultrasonic transducers used for inspection of solid objects with curved surfaces. Specifically, the inspection utilizes the immersion technique. In this technique, an object is placed in liquid to improve coupling of the ultrasonic wave energy into the part. Ultrasonic energy focused beneath the surface of the inspected object is also addressed, improving sensitivity of inspection in that region.

When an ultrasonic inspection is performed, a transducer is calibrated on a flat surface with the same material to be inspected. A set of inspection parameters, such as gain, operating frequency and water-path, are set and calibrated to the flat-top block. The inspection parameters are used to inspect production hardware. In many cases, the same parameters are used to inspect through curved entry surfaces.

Passing the sound beam through a convex surface decreases the effective sensitivity. However, for a concave surface, the sensitivity of the sound beam increases and then starts to sharply decrease after a certain depth. The effect of a curved surface on inspection sensitivity is very complex. It is difficult to compensate for curved surface effect and keep the same sensitivities as for the flat entry surface.

Many governing agencies and product specifications require that attention be paid to entry surface effects. It is also often required that a curved specimen be used to qualify the inspection process. However, procedure time and cost. and degree of surface curvature variations within a single region make compliance difficult.

It would be desirable then to have a transducer capable of inspecting a part with any curved direction of entry surface.

BRIEF SUMMARY OF THE INVENTION

Mathematical calculation shows that convex surfaces, not just concave, need compensation to get inspection results like a flat surface. However, concave surfaces present complications in that intensity of the sound beam increases then sharply decreases after a certain depth. Hence, a saddle shaped aspherical transducer with a curved element is calculated. The transducer is particularly suited for inspecting a part with a doubly curved entry surface. The aspherical transducers make ultrasonic inspection possible on highly curved parts, by compensating for the entry surface of the part.

An ultrasonic inspection element and method of fabrication are provided for ultrasonic inspection. Specifically, a method is provided for determining the radii of an aspherical transducer. First, various points on a transducer surface are located. These points include where a ray starts, passes through a water medium and a water-metal boundary, and runs into a desired focal point in the material to be inspected. Next, the points are fitted onto a cylindrical surface for ease of transducer fabrication.

Accordingly, the present invention provides an effective technique for performing ultrasonic inspection, particularly of curved entry surface parts.

DETAILED DESCRIPTION OF THE INVENTION

Figure 1:
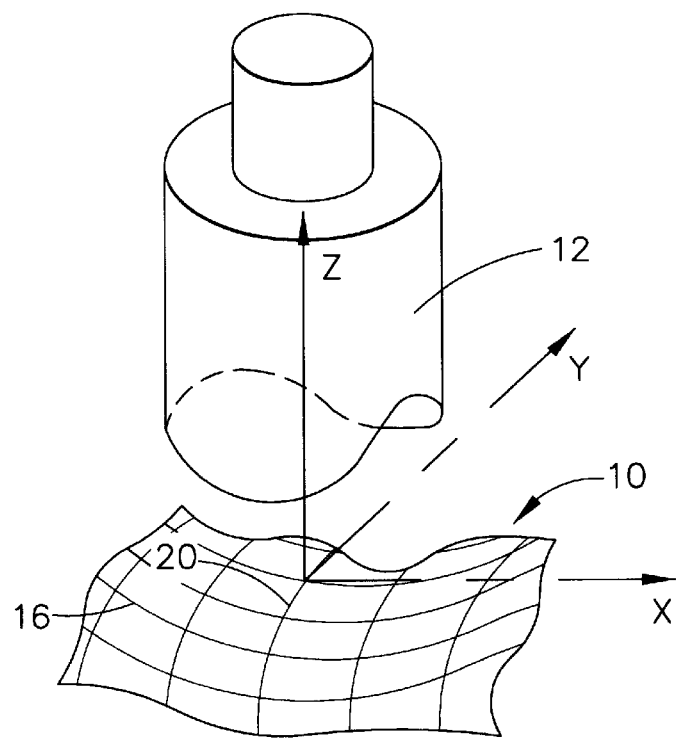
FIGS. 1–3 illustrate the curvature structure of a transducer, relative to the curved entry surface of the part to be inspected.

The present invention proposes a curved spherical transducer for inspecting curved entry surface parts. A determination is made of the required transducer radius for penetrating into a designated inspection depth through a curved surface. The curvature of the transducer, therefore, is calculated based on the sonic energy penetration required of the transducer.

Referring to the drawings, for a part 10, to be inspected, the curvature of the spherical transducer 12 is designed in two axes, X and Y, independently. The X-directional curvature 14, FIG. 2, is computed to accommodate the primary curvature 16 of the part 10 to be inspected, FIG. 1. The Y-directional curvature 18, FIG. 3, is computed to accommodate the secondary curvature 20 of the part 10.

Figure 2:
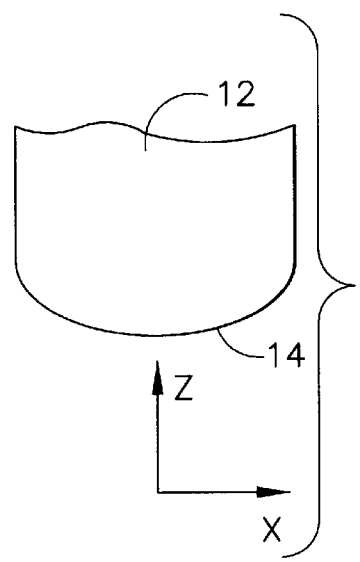
Figure 3:
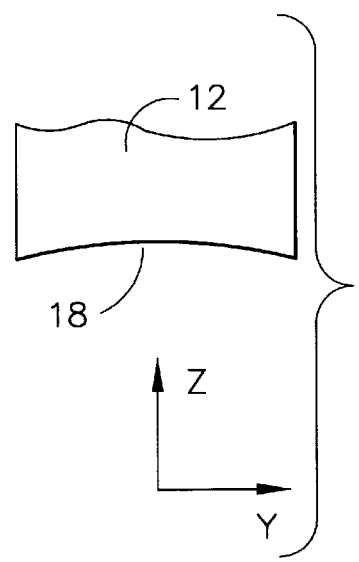

The curvature of the aspherical transducer preferably imitates the curvature of the part, as illustrated in FIGS. 1–3. The curvature can be computed using any suitable method, such as the following two-step process. The first step is to find various points on a transducer surface. These points include where a ray starts, passes through a water medium and a water-metal boundary, and runs into a desired focal point in the material to be inspected. This is best illustrated in FIG. 4.

Figure 4:
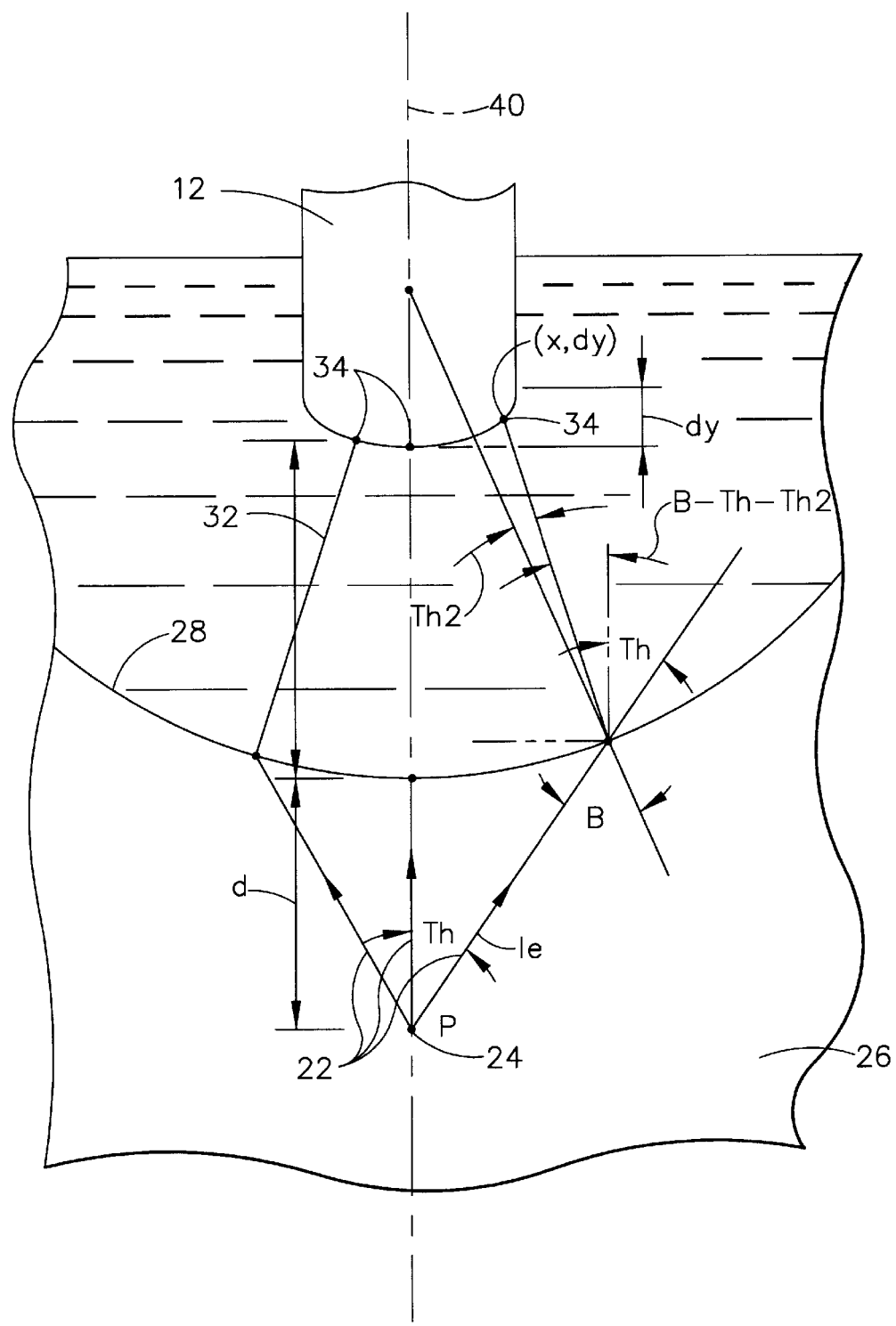
FIG. 4 illustrates a curved entry transducer of the present invention relative to a curved entry surface.

In order to find the points on the transducer in FIG. 4, an array of rays 22 starts from a designated focal point 24 inside the material 26. The rays 22 propagate toward the material surface 28, in the direction of the arrows of rays 22. The rays 22 then cross the material-water boundary 28, where their angles of propagation are changed. The rays 22 pass through water 32. Finally, the rays 22 reach points 34 on the transducer 12 surface.

The angles of rays 22 after the material-water boundary are determined by the velocity ratio of the material and water. Snell's Law describes this. The distance from the boundary to the transducer can also be computed. This computation is $T_{13}$total minus $T_{13}$material. $T_{13}$total is sonic travel time from the transducer 34 to a focal point 24 inside the material 26 through the center axis 40 of the transducer and material. $T_{13}$material is sonic travel time from a focal point 24 inside the material to the material surface 28. $T_{13}$water is sonic time travel from the material surface to a point on the transducer surface. Focal point 24 is a predetermined design focal point of a new transducer.

Multiple points on a transducer surface can be determined in such a manner that, regardless which path a ray takes, travel time from focal point to transducer surface point equals $T_{13}$total. If the transducer points that meet the Fermat's principle are found, they lie on an aspherical locus.

One example of a derivation to find a point (x, dy) on a curved element transducer is as follows:

x is distance in radial direction between the center axis and a point for the curved element;

dy is the distance in a central axis direction between a middle point of the transducer and a point for the curved element;

R is the radius of a part;

d is the focal depth inside the part;

wp is the waterpath between the transducer and part;

trans$_{13}$radius is the curvature of the transducer;

PI=3.14159;

cw=0.1481 cm/microsecond or acoustic velocity in water; and cm=0.0617 cm/microsecond or acoustic velocity in Titanium.

In accordance with this derivation, the ray starts from designated focal point P in FIG. 4.

For each chosen angle Th,

Sin(PI−B)=((R+D)*Sin(Th)), therefore, B=PI*Asin((R+d)/R*Sin(Th)).

Also, le*Sin(Th)=R*Sin(B−Th)

therefore, le=R*(Sin(B−Th)/Sin(Th)).

And

Th2+Asin(cw/cm*Sin(B)) from Snell's Law.

Then applying Fermat's principle,

Ray's travel time off axis=Ray's travel time on axis, so le/cm +{[(wp+d−le*Cos(Th))+dy]/[Cos(B−Th−Th2)]}*(1/cw)=(wp/cw)+d/cm), which can be solved for dy:

dy=(le/cm+wwp/cc−Twm)/(−icc)

where cc=cw*Cos(B−Th−Th2)

and wwp=wp+d−le*Cos(Th)

and Twm=(wp/cw)+(d/cm).

Also, x is the distance between the center of the transducer and a point where the dy is computed, and is computed geometrically:

x=le*Sin(Th)−((wp+d−le*cos(Th)+dy)*tan(B−Th).

Even though the points determined are optimal points for a transducer design, it can be impractical to fabricate a transducer with a calculated complex geometry. Therefore, the second step of the transducer design is to fit the points onto a cylindrical surface. A cylindrical surface is easier to machine than a non-cylindrical surface, best fitting the computed points above. With proper application, the performance of the transducer is not compromised.

After the radius of curvature is found which approximates the aspherical surface, and the curve fitting, this cylindrical curvature of the transducer has to be verified. The verification determines whether rays from the new curvature would be focused on the designated point 24 in the material. Therefore, the rays from the new circular surface are computationally back-propagated into water. The back-propagation is through the water-material boundary and into the material. If all the rays focus onto the designated point 24, the fitted circular radius is the correct curvature of the transducer. If the back-propagated focal point is away from the designated focal point, a new radius of a transducer curvature is computed after the start point, P, in FIG. 4, is displaced. The displacement is with a small increment or decrement, depending on a trend. The trend is the differential direction between the back-propagated focal point and the predetermined focal point 24. It is noted that the same two steps used to find the X-axis curvature could be used to find the Y-axis curvature.

Figure 5:
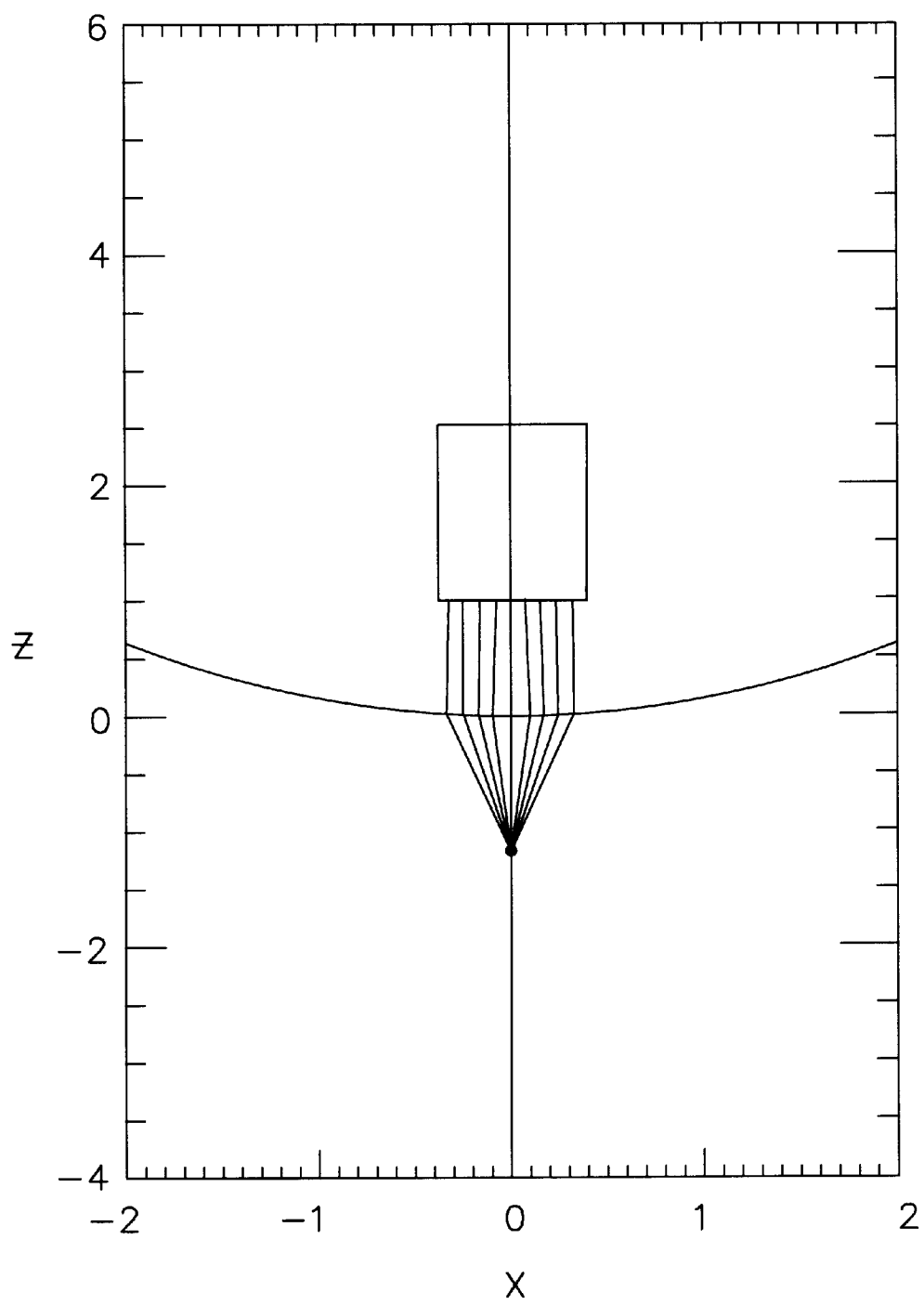
FIGS. 5 and 6 are graphical representations of the transducer design, on the X-axis and Y-axis for a curved entry surface with different X, Y curvature, respectively.
Figure 6:
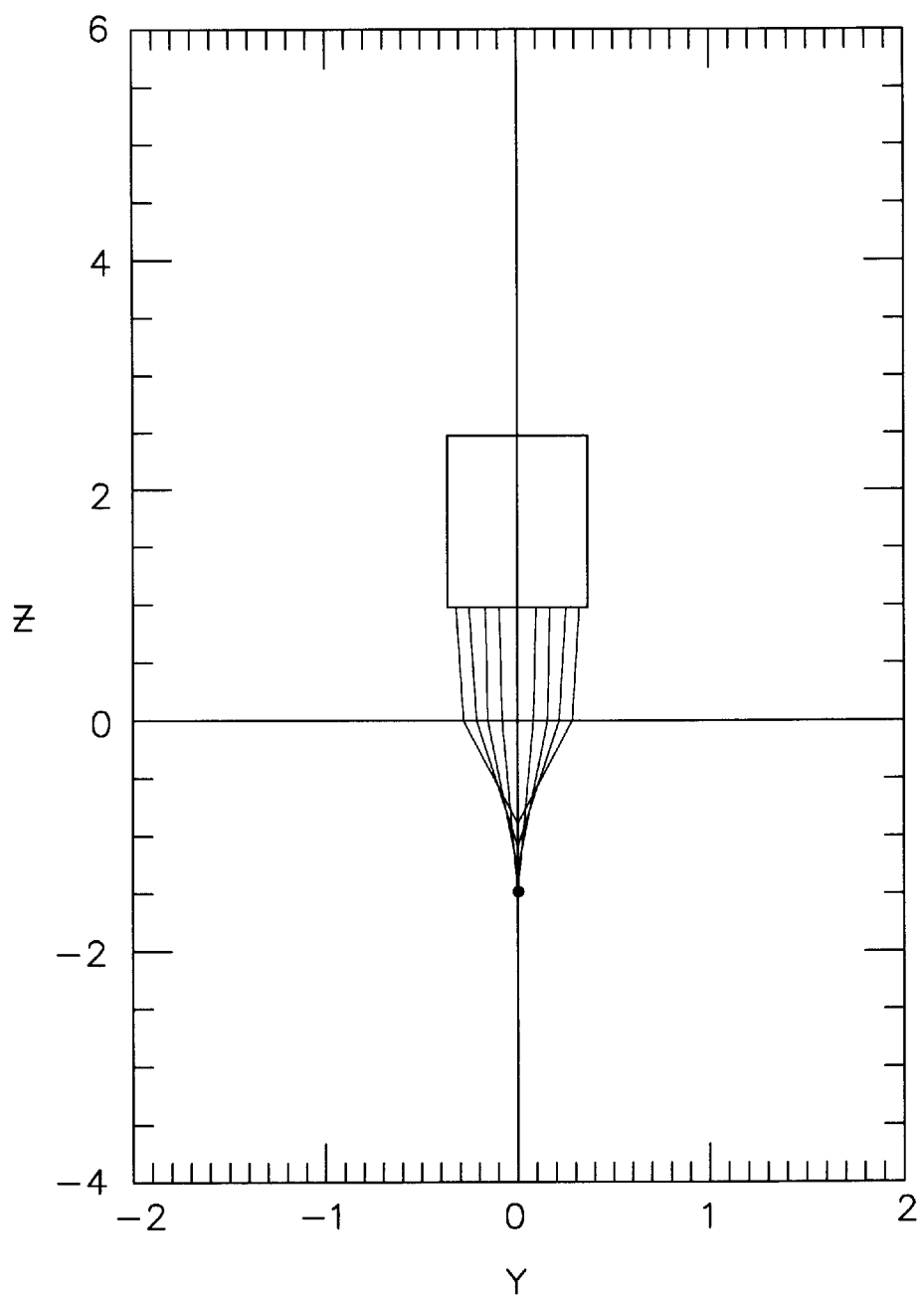

As seen in FIGS. 5 and 6, the radius of the transducer 12 would be concave or convex, depending on the severity of curvature of part 10 or material 26. After the radii of the transducer curvature are defined, the transducer can be fabricated. Fabrication starts with a machined epoxy mold, for use as a backing to absorb undesired sound. The backing for the curvature correction transducers is preferably a good absorber and scatterer of acoustic energy. It also preferably has the ability to be shaped as needed to obtain a particular focus. One suitable epoxy is commercially available Astro 3060 epoxy.

Aluminum foil is then epoxied to the convex and concave surfaces for a backing electrode. The backing electrode preferably reflects most of the acoustic energy away from the backing. This increases the amount of useful energy and reduces that which gets into the backing. Acoustic energy in the backing can generate an unwanted echo. A suitable backing electrode material is 0.0127 cm aluminum and can be shaped as required to fit the backing and then bonded to the backing.

Polyvinylidene fluoride (PVDF) film is then bonded or otherwise attached on top of the backing electrode as an active element. The film is metallized, typically with around 1500A to 2000A of gold. The metallization method is preferably vacuum evaporation. This surface is a ground electrode. Copper tabs and flexible wire can be used to make contact to ground and the rf connector.

The backing can then be bonded into another cylinder to act as a mechanical housing. Electrical connections are then made to the backing electrode and the ground electrode.

The aspherical transducer can be used to inspect parts with a combination of convex and concave curvatures. Dual curvatures can be applied to cancel the curvature effect of the part. The invention preferably uses PVDF technology, to avoid using a focusing lens in the transducer. Internal vibration of such a lens may distort the ultrasonic signal.

While the invention has been described with reference to a preferred embodiment, it will be understood by those skilled in the art that various changes may be made and equivalents may be substituted for elements thereof without departing from the scope of the invention. For example, this process can be applied in various environments. The process can be applied to turbine blades with laser drilled holes. The process can also be applied to any part that has laser expulsion on its surface and around the hole. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for designing an ultrasonic transducer to focus energy at the desired depth in a part with a non planar surface, the transducer projecting sound rays and having a radius, the method comprising the steps of:

a. determining an ideal surface geometry of the transducer;

b. adapting the determined ideal surface geometry to a nearest approximation circular profile for transducer fabrication without compromising focusing capability at a desired focal point;

c. back-propagating rays from the transducer into the determined focal point;

d. adjusting the radius of the transducer responsive to focus location of the transducer rays relative to the desired focal point; and e. repeating the determining, adapting, back-propagating and adjusting steps until the back-propagated rays are focused at the determined focal point.

2. A method as claimed in claim 1 wherein the step of determining an ideal surface geometry of the transducer comprises the step of mathematically determining an ideal surface geometry of the transducer.

3. A method as claimed in claim 2 wherein the step of mathematically determining an ideal surface geometry of the transducer comprises the step of using ray-trace.

4. A method as claimed in claim 3 wherein the step of using ray-trace comprises the step of requiring time of flight of energy from focal point to a surface of the transducer to be constant across said surface.

5. A method as claimed in claim 1 wherein the step of adapting the determined ideal surface geometry to a nearest approximation circular profile comprises the step of fitting points on a computed aspherical surface of the transducer to a cylindrical line for ease of fabrication.

6. A method for designing an ultrasonic transducer assembly to focus energy at the desired depth in a part with a non planar surface, the method comprising the steps of:
   a. providing a transducer element, the transducer element projecting a sound beam and having a radius;
   b. determining an ideal surface geometry of a lens to be attached to a face of the transducer element;
   c. adapting the determined ideal surface geometry of the lens to a nearest approximation circular profile for ease of fabrication of the transducer element without compromising focusing capability at a desired focal point;
   d. back-propagating the rays from the transducer element into the determined focal point;
   e. adjusting the radius of the transducer element responsive to a focus location of the transducer element rays relative to the desired focal point; and
   f. repeating the determining, adapting, back-propagating and adjusting steps until the back-propagated rays are focused at the desired focal point.

7. A method as claimed in claim 6 wherein the step of determining an ideal surface geometry of the transducer comprises the step of mathematically determining an ideal surface geometry of the transducer.

8. A method as claimed in claim 7 wherein the step of mathematically determining an ideal surface geometry of the transducer comprises the step of using ray-trace.

9. A method as claimed in claim 8 wherein the step of using ray-trace comprises the step of requiring time of flight of energy from focal point to a surface of the transducer to be constant across said surface.

10. A method as claimed in claim 6 wherein the step of adapting the determined ideal surface geometry to a nearest approximation circular profile comprises the step of fitting points on a computed aspherical surface of the transducer element to a cylindrical line for ease of fabrication.

11. A method as claimed in claim 6 wherein the transducer element comprises a plastic lens.

* * * * *